(12) United States Patent
Andrews

(10) Patent No.: US 8,383,165 B1
(45) Date of Patent: Feb. 26, 2013

(54) COMPOSITION AND METHOD FOR FERTILITY THERAPY USING NUTRITIONAL SUPPLEMENTS

(75) Inventor: Kelly Andrews, Bellingham, WA (US)

(73) Assignee: Fairhaven Health, LLC, Bellingham, WA (US)

( * ) Notice: Subject to any disclaimer, the term of this patent is extended or adjusted under 35 U.S.C. 154(b) by 469 days.

(21) Appl. No.: 12/551,465

(22) Filed: Aug. 31, 2009

(51) Int. Cl.
*A61K 36/00* (2006.01)
*A61K 36/87* (2006.01)
*A61K 36/16* (2006.01)
*A61K 36/254* (2006.01)

(52) U.S. Cl. .......................... 424/725; 424/766; 424/752

(58) Field of Classification Search .................. None
See application file for complete search history.

(56) References Cited

U.S. PATENT DOCUMENTS

| | | | |
|---|---|---|---|
| 5,904,924 A * | 5/1999 | Gaynor et al. | 424/195.17 |
| 2003/0224070 A1* | 12/2003 | Sweazy et al. | 424/725 |
| 2007/0104801 A1* | 5/2007 | Cecchi et al. | 424/641 |
| 2008/0139504 A1* | 6/2008 | Van Den Elshout et al. | 514/59 |
| 2009/0170774 A1* | 7/2009 | Ramaekers | 514/12 |

* cited by examiner

*Primary Examiner* — Qiuwen Mi
(74) *Attorney, Agent, or Firm* — Nancy Lord, Ltd.

(57) ABSTRACT

A new composition and method are described for female fertility therapy. In one alternative, the composition utilizes three nutritional supplements, grape seed, para amino-benzoic acid (PABA), and red clover. When it is administered to females as fertility therapy following the recommended dosage, interleukin-6 is inhibited by the dose of grape seed, blood levels of folic acid are supported by the dose of PABA, and the dose of red clover provides phytoestrogenic isoflavones.

4 Claims, No Drawings

COMPOSITION AND METHOD FOR FERTILITY THERAPY USING NUTRITIONAL SUPPLEMENTS

FIELD OF INVENTION

This invention is directed to fertility-enhancing dietary and nutritional supplement compositions for human male infertility therapy and to methods employing these compositions. By providing these supplements, the invention will provide a fertility-enhancing composition for human female fertility therapy is taught, comprising an interleukin-6 inhibiting dose of grape seed, a dose of para-amino benzoic acid (PABA) sufficient to support optimal blood levels of folic acid, and a dose of red clover comprising phytoestrogenic isoflavones. The invention will provide, unlike others, a regimen of supplements that will provide the reproductive system with a continued supply of these nutrients, where in the body will manufacture certain agents that will boost the reproductive system and will assist the user to attain conception within a few months.

BACKGROUND OF THE INVENTION

Infertility is defined by most authorities as the inability to achieve a pregnancy after one year of unprotected intercourse. Conception is normally achieved within 12 months in 80-85 percent of couples using no contraceptive measures; thus an estimated 15 percent of couples attempting their first pregnancy will have difficulty conceiving.

Grape Seed and Endometriosis

Resveratrol, a potent isoflavone found in grape seed, is best known for its potential life extending properties as shown by studies in *Drosophila Megaloblaster* (fruit fly) and budding yeast, *Saccharomyces cerevisiae*. Canton-S flies cultured on food containing 200 M resveratrol showed an increase in average lifespan of 17% for females and 10% for males and an increase in maximum lifespan of 22% and 20% for females and males, respectively.

Although it is known to exert pleiotropic effects the lifespan extending effect of resveratrol is thought to be mediated by means of the activation of the histone deacetylase Sir2. Sir2 has been implicated in lifespan extension of yeast, nematodes, and fruit flies, and it has been proposed to mediate some of the effects of calorie restriction. Consistent with the importance of Sir2 activity in lifespan determination, scientific data showed that treatment of flies with the Sir2 inhibitor sirtinol leads to shortening of lifespan Bauer, et a., 101(35) Proc Natl Acad Sci USA 12980-12985 (2004).

Resveratrol has also been shown to protect ovarian follicles be antagonizing the aryl hydrocarbon receptor gene that sensitizes them to toxic polycyclic aromatic hydrocarbons (PAHs). Researchers provided molecular evidence for a pathway involved in the elimination of the female germline due to prepregnancy and/or lactational exposure to (PAHs), environmental toxicants found in cigarette smoke. Ovaries of offspring born to mice exposed to PAHs contained only a third of the ovarian follicle pool compared with offspring of unexposed female mice. Activation of the cell death pathway in immature follicles of exposed females was mediated by the aryl hydrocarbon receptor (Ahr), as ovarian reserve was fully rescued by maternal cotreatment with the Ahr antagonist, resveratrol, or by inactivation of the Ahr gene. Furthermore, in response to PAHs, Ahr-mediated activation of the harakiri, BCL2 interacting protein (contains only BH3 domain), was necessary for execution of cell death. Jurisicova, et al 117(12) J Clin Invest 117(12):3971-8 (2007).

One study found, however, that grape seed extract increased IL-6 levels in cultured neurons. Grape polyphenols are known to protect neurons against oxidative stress. Grape seed extract (GSE) from "Koshu" grapes (*Vitis vinifera*) containing a variety of polyphenols, was subjected transcriptome analysis to determine the effects of GSE on primary cultures of astrocytes in the hippocampus. GSE upregulated various mRNAs for cytokines, among which interleukin-6 (IL-6) showed the biggest increase after treatment with GSE. The GSE-evoked increase in IL-6 mRNAs was confirmed by quantitative RT-PCR. IL-6 proteins were detected by ELISA in the supernatant of GSE-treated astrocytes and an oxidative stress-induced neuronal cell death model in vitro using a neuron rich culture of the hippocampus was developed. Treatment of the neurons with $H(2)O(2)$ caused neuronal cell death in a time- and concentration-dependent manner. Exogenously applied IL-6 protected against the $H(2)O(2)$-induced neuronal cell death, which was mimicked by endogenous IL-6 produced by GSE-treated astrocytes. Taken together, GSE acting on astrocytes increased IL-6 production, which functions as a neuroprotective paracrine, could protect neuronal cells from death by oxidative stress. Fujishita, K, et al, Cell Mol. Neurobiol. 2009 Apr. 21. [Epub ahead of print].

The majority of research shows the contrary. Over recent years, resveratrol, found in grape seed, has been shown to inhibit levels of Interleukin-6 (IL-6) associated with infertility particularly that resulting from endometriosis. Endometriosis is a benign estrogen-dependent gynecological disease, which affects approximately 10% of women of reproductive age, is characterized by the presence of endometrial tissue outside the uterine cavity, and is associated with pelvic pain, dysmenorrea and infertility. Despite all the research accumulated over the years, the etiology and the pathogenesis of endometriosis are still unclear. Minici, et al, 23(3) Human Reproduction 23(3):530-537 (2008). It has been found in the majority of women with a regular menstrual cycle and infertility. Kunz, G, et al, 20(8) Hum Reprod: 2309-16 (2005).

Kunz, et al, Id., studied 227 women with regular menstrual cycles (mean 29 days, range 21-28) aged 17-46 years (mean 32.5) each after giving informed consent. Together with their male partners, they had a history of infertility prompting them to have a sterility work-up and subsequent treatment in Dr. Kunz' infertility clinic. Of these patients, 160 women (aged 17-46 years; mean 32.3) with a history of infertility of 1-13 years (mean 3.6) were suffering from endometriosis as demonstrated by laparoscopy. Almost one half of these patients presented with minimal or mild endometriosis (n=81) and the rest with moderate or severe endometriosis (n=79), according to the revised classification of the American Society of Reproductive Medicine (ASRM). No additional factors responsible for their female infertility could be identified.

Endometriosis is so highly associated with elevated levels of the inflammatory cyokine that elevated levels of IL-6 in women with endometriosis is used as reliable non-invasive marker for the disease. A serum IL-6 threshold of 25.75 pg/ml afforded a sensitivity of 75% and specificity of 83% in the diagnosis of MM endometriosis. Sensitivity and specificity for CA-125 in the diagnosis of MS endometriosis, using 35 IU/ml as the cut-off value, were 47% and 97%, respectively. Martinez, S et al, 22(3) Hum Reprod 836-42 (2007).

The prevalence of adenomyotic lesions in all 160 women with endometriosis was 79%. In women with endometriosis below an age of 36 years and fertile partners, the prevalence of adenomyosis was 90% (P<0.01) With a prevalence of up to 90%, uterine adenomyosis is significantly associated with pelvic endometriosis and constitutes an important factor of sterility in endometriosis presumably by impairing uterine sperm transport. Kunz, G, et al, 20(8) Human Reproduction 2309-2316 (2005)

Even in the absence on adenomyotic lesions, Interleukin-6 (IL-6) that has a negative impact on sperm motility. Even in the absence on adenomyotic lesions, Interleukin-6 (IL-6) that has a negative impact on sperm motility. The expression of IL-6 and its receptor was detected in human granulosa cancer cells. Estradiol secretion was significantly inhibited by adding IL-6, which also suppressed aromatase activity to 50% of the control. The findings demonstrated that IL-6 may reduce estrogen production in human granulosa cells and may support the notion that IL-6 is related to impaired estrogen biosynthesis in patients with endometriosis. Deura, et al, 83 Suppl 1 Fertil Steril 1086-92 (2005).

Other grape polymers have found to have similar activities in modulating IL-6. Researchers examined the potential antioxidant activity and the immunopharmacological activity of new epicatechin conjugates obtained by depolymerization of grape polymeric flavanols in the presence of cysteamine or cysteine and with or without gallate. The compounds studied were (−)-epicatechin (1), cysteinyl-epicatechin (2), cysteamine-epicatechin (3), (−)-epicatechin gallate (4), cysteinyl-epicatechin gallate (5), and cysteamine-epicatechin gallate (6) When incubated with an erythrocyte suspension, flavanols protected the erythrocyte membrane from hemolysis induced by 2,2'-azobis(2-amidinopropane)dihydrochloride, an azo free-radical initiator. All the epicatechin derivatives tested were more efficient as antioxidant than epicatechin. The compounds were tested for their capacity to modulate IL-1beta and IL-6, which are the main cytokine factors influencing the acute phase of the inflammatory response. (−)-Epicatechin and its related compounds inhibited the production of IL-1beta and IL-6 in whole blood incubated in the presence of *Escherichia coli* lipopolysaccharide. Mitjans, M, et al, 52(24) J Agric Food Chem 7297-9 (2004).

Other researchers using transvaginal ultrasound examinations measured serum IL-6 concentrations in 14 patients with ovarian endometrioma and 4 patients with benign gynecologic disease without endometriosis. IL-6 was significantly higher in patients with endometrioma than in those without endometriosis at the time of diagnosis. The mean serum IL-6 concentration significantly decreased after the operation for the disease. Yoshida, S, et al, 54 Suppl 1 Gynecol Obstet Invest 24-7; discussion 27-9 (2002).

Detailed studies have demonstrated the effects of various other types of grapes on IL-6 in the context of the mast cell-mediated allergy model in vitro. Kim, S, Kwoh, T, and Shin, T, 233 Experimental Biology and Medicine 192-199 (2008). In the Kim study, a preparation of Methanol Extract of *V. amurensis* (MEVA) was prepared and assays performed for its effect on TNF-{alpha}, IL-6, and IL-8 Secretion. TNF-{alpha}, IL-6, and IL-8 secretion was measured by modification of an enzyme-linked immunoabsorbent assay (ELISA). Cultured cells treated with the extract showed dose-dependently inhibited the secretion of TNF-{alpha}, IL-6, and IL-8 in PMACI-stimulated HMC-1 cells.

Similar findings were observed in animals. The inhibition pattern on the release of IL-6 was similar to that seen with TNF-alpha. In a related in vivo study, rats were fed a diet containing 5% (wt/wt) dried muscadine grape skins (*Vitis rotundifolia*) for 14 days and then were injected with carrageenan in the foot pad. After 3 h, paw edema was measured and the rats on the grape skin diet had approximately 50% less paw edema than controls (P<0.05). These results demonstrate that the muscadine grape skin powder possesses significant in vitro and in vivo antiinflammatory properties. Greenspan, et al 53(22) J Agric Food Chem 8481-4 (2005).

Para-aminobenzoic Acid (PABA) and Folate Levels

In addition to the well-established association between folic acid deficiency during pregnancy and neural tube and other birth defects, Wolff, T, et al, 150(9) Ann Intern Med 632-9 (2009), the intake of folic acid supplements, with or without additional multivitamins, is associated with a reduction in infertility disorder due to ovulatory disorder. Chavarro J E, et al, 89(3) Fertil Steril 89(3):668-76 (2008). Chavarro, et al, studied 438 women with reported infertility due to ovulatory disorder for 8 years. There was an inverse association between frequency of multivitamin use and ovulatory infertility. The multivariate-adjusted relative risk (95% confidence interval) of ovulatory infertility was 0.88 (0.60, 1.28) for women consuming 2 tablets/week or less, 0.69 (0.51, 0.95) for women consuming 3 to 5 tablets/week and 0.59 (0.46, 0.75) for women consuming 6 or more tablets/week, when compared to women who did not use these supplements (P, trend<0.001). Folic acid appeared to explain part of the association between multivitamin supplement use and risk of ovulatory infertility. Adjusting for multi-vitamin use attenuated, but did not vitiate, the association with folic acid intake alone. The researchers noted that supplementation with folic acid by itself or as part of a multivitamin has been shown to reduce the risk of neural tube defects and may prevent other congenital malformations, and suggested that women planning to become pregnant should consider taking a multivitamin as this may also help them to become a pregnant.

Reduced levels of folic acid or folate and increased homocysteine are associated with infertility. Possible mechanisms of the deleterious effects of folate deficiency and homocysteine accumulation on female fertility include, as in the male, reduced cell division (e.g. of oogonia during oogenesis or of granulosa cells during folliculogenesis), inflammatory cytokine production, altered NO metabolism, oxidative stress, apoptosis and defective methylation reactions. Forges, T, et al, 13(3) Hum Reprod Update 225-38 (2007).

While opposite results have been observed by researchers, Avivia and Boxtel, 11(6) Trop Med Int Health 11(6):804-8 (2006), there are several reports of increased folic acid turnover during pregnancy and a resulting deficit. Gregory, J F, et al, J Nutr 131(7):1928-37 (2001); Higgins, J R, et al, 107(9) BJOG 107(9):1149-54 (2000). Para-amino benzoic acid (PABA) is metabolized into folic acid both by polymorphonuclear neutrophils, Sagone A L Jr, Husney R M & Davis W B 14(1) Free Radic Biol Med 27-35 (1993) and gut bacteria, Camilo E, et al, 110(4) Gastroenterology 991-8 (1996). Hence, the supplementation of PABA in addition to the standard folic acid supplementation provides a pool of folic acid precursor that may be utilized to replenish catabolized folic acid.

Red Clover and Phytoestrogens

The need for adequate levels of estradiol to conceive and maintain pregnancy is well-established, and serves as the basis for several of the pharmacological treatments for infertility. Ming-fang Miao and He-feng Huan, 10(1) J Zhejiang Univ Sci B 10(1): 35-45 (2009). The isoflavone genistein GEN is a saponin found in soy (*Glycine max*) and red clover (*Trifolium pratense*). The estrogenic activity of GEN is known, and it is widely advertised as a phytoestrogen useful in alleviating climacteric complaints and other postmenopausal disorders. Knowledge of effects of long-term administration of GEN in laboratory animals is scarce, and effects in the uterus and mammary gland after long-term administration have not been studied. The uterus and mammary gland are known to be negatively influenced by estrogens used in pharmaceutical hormone therapy. In rats treated with either of estrogen doses or the high GEN doses, researchers found increased uterine weight, and histologic analysis showed estrogen-induced features in the uteri. In vaginae, these same treatments induced hyperplastic epithelium compared with the atrophic controls. The endometrium was composed of cuboidal inactive cells, and the connective tissue was an unorganized lax syncytium of round nuclei. No mitotic activity was detected in epithelial cells. Serum levels of luteinizing hormone were decreased by estrogen but not by GEN. Rimoldi, et al, 115 (S-1) Environ Health Perspect 62-68 (2007).

The relative oestrogenic activities of 0.1 g each of extracts of phytosterol, soy isoflavone, red clover, kudzu and soybean extracts were determined using this assay and found to be equivalent to 212, 1, 3.2, 132 and 1025 nM of 17 beta-estradiol, respectively. Bennetau-Pelissero, et al C 15(1) Phytochem Analysis 40-5 (2004).

*Vitex agnus-castus* and Luteal Phase Progesterone

Low levels of progesterone can result in infertility along with short menstrual cycles as the progesterone is required to maintain the corpus luteum prior to fertilization. Chimpanzees in Gombe National Park consume fruits of *Vitex fischeri* during a short annual fruiting season. This fruit species is a member of a genus widely studied for phytoestrogen composition and varied physiological effects. One particularly well-studied species, *V. agnus-castus*, also known as chaste-berry, is noted for its documented effects on female reproductive function evidenced in increased progesterone levels and consequent regulation of luteal function. Thompson, E M, 70(11) Am J. Primatol. 2008 November; 70(11):1064-71. (2008)

Results of a small clinical trial involving 96 women with fertility disorders (38 women with secondary amenorrhea, 31 with luteal insufficiency, and 27 with idiopathic infertility) suggested that patients receiving chasteberry achieved pregnancy more readily than did women in the placebo group. The subjects received chasteberry or placebo twice daily for three months. Hormone levels did not differ, but in women with amenorrhea or luteal insufficiency, pregnancy occurred in the active treatment group more than twice as often as in the group receiving placebo. However, the total number of patients conceiving was small (15 women), the treatment was only administered for three months, and the product used contained five additional herbs. Roemheld-Hamm, B, 72 Am Fam Physician 821-4(2005).

In another small study involving 52 patients with luteal phase defects, women in the active treatment group were found to have reduced prolactin release, normalized luteal phases, improved luteal phase progesterone synthesis, and increased luteal phase estradiol. This study appeared to support the use of chasteberry for luteal phase disorders, but the actual effect on fertility was not mentioned. A recent double-blind placebo-controlled pilot study 27 of 30 women showed an increasing trend in midluteal phase progesterone level and an increased number of pregnancies in the 15 women who took a nutritional supplement containing chasteberry for five months. Roemheld-Hamm, B, 72 Am Fam Physician 821-4 (2005).

Even in wild chimpanzees, hyperprogesteronemia has been associated with *Vitex fischeri* consumption. Chimpanzees in Gombe National Park consume fruits of *Vitex fischeri* during a short annual fruiting season. This fruit species is a member of a genus widely studied for phytoestrogen composition and varied physiological effects. One particularly well-studied species, *V. agnus-castus*, is noted for its documented effects on female reproductive function, evidenced in increased progesterone levels and consequent regulation of luteal function. Researchers examined reproductive hormone levels in both male and female chimpanzees during a 6-week period of intense *V. fischeri* consumption. *V. fischeri* consumption was associated with an abrupt and dramatic increase in urinary progesterone levels of female chimpanzees to levels far exceeding the normal range of variation. Female estrogen levels were not significantly impacted, nor were male testosterone levels. Thompson, E M, 33(4) Clin Exp Obstet Gynecol 205-8 (2006).

An Agnus castus-containing homeopathic preparation was investigated in Germany in 67 women with fertility disorders who received 50 drops of Phyto Hypophyson L or placebo 3 times a day over 3 months or 3 cycles. The outcome measure were spontaneous menstruation, improved concentration of progesterone in the luteal phase, shortening of the cycle, and earlier ovulation. Pregnancy was achieved in 38 out of 67 women, more often from women with oligomenorrhea in the Phyto Hypophyson L group compared to the placebo group (82 versus 45%, p=0.021). However, there was no significant effect when viewing the whole group. The baby take-home rate during therapy and 6 months after the end of therapy showed a ratio of 6:2 (18.7:6.4%), which was not significant. Furthermore, in the oligomenorrhea verum group we observed a significant increase of progesterone during the luteal phase compared to the oligomenorrhea placebo group. Bergmann, 7(4) Forsch Komplementarmed Klass Naturheilkd. 190-9 (2000).

In another German study of another *Vitex agnus castus* preparation and placebo, subjects were given 20 mg of either the *Vitex agnus-castus* or placebo. Aim of the study was to prove whether the elevated pituitary prolactin reserve can be reduced and deficits in luteal phase length and luteal phase progesterone synthesis be normalized. Blood for hormonal analysis was taken at days 5-8 and day 20 of the menstrual cycle before and after three month of therapy. Latent hyperprolactinaemia was analysed by monitoring the prolactin release 15 and 30 min after i.v. injection of 200 micrograms TRH. 37 complete case reports (placebo: n=20, Vitex n=17) after 3 month of therapy were statistically evaluated. The prolactin release was reduced after 3 months, shortened luteal phases were normalised and deficits in the luteal progesterone synthesis were eliminated. These changes were significant and occurred only in the group treated with *Vitex agnus-castus*. Milewicz, A, 43(7) Arzneimittelforschung 752-6 (1993).

*Eleuthero senticosus* and phytoestrogens

There are a group of so-called tonic remedies in Far Eastern medicine which are traditionally viewed as harmonizing or adjustive. Ginseng and eleutherococcus are the best known, and there is evidence that they increase arousal, stamina and stress resistance. We have attempted to explore the relationship between the behavioral and the stress effects, and to relate this to traditional concepts. In one series of experiments mice were given ginseng throughout their lifespan. At intervals their behavior response to mild stress was examined and found to be exaggerated compared to controls without ginseng. However, normal ambulatory behavior in the absence of stress was unaffected. A second series of experiments indicated that the binding of corticosteroid to certain brain regions was increased in adrenalectomized rats given ginseng saponin, compared to saline treated controls. This can be interpreted as a result of an increase in hypothalamic-pituitary-adrenal sensitivity caused by ginseng saponin. This is in accord with traditional concepts of the use of these remedies. Fulder S J, 9(2) Am J Clin Med 112-8 (1981).

*Eleuthero senticosis*, also known as ginseng, has been shown to attenuate nerve grown factor, associated with polycystic ovaries, in female rats. Polycystic ovary was fully developed in rats with a single intramuscular injection of estradiol valerate. Increased expression of nerve growth factor (NGF) was noted in the ovaries and the brain of rats with polycystic ovaries. Korean red ginseng total saponins administration attenuated NGF expression in the ovaries but not in the brain. Pak, et al 84 Supp 2 Fertil Steril 1139-43 (2005). Ginseng has also been shown to produce increased embryonic growth at 50 micrograms/ml and hindbrain, midbrain and caudal neural tube at 100 micrograms/ml with Ginsenoside Rc and the pGPx mRNA level increased at all doses. Lee, et al, 54(3) J Reprod Devel 164-70 (2008).

Eleuthrococcus has also been shown to protect the developing embryo. Preventive administration of Eleutherococcus extract during prenatal and pre-embryonic periods of development prevents embryotoxic effect of subsequent treatment of pregnant rats with ethanol and sodium salicylate. Eleutherococcus abolishes embryotoxic and teratogenic effects of ethanol manifested against the background of experimental syndrome of iron deficit in pregnant females. Mechanism of its antiteratogenic action is probably based on stimulation of cell detoxification mechanisms, increase in energy potential of cells, as well as on stabilization of structural and functional state of cell membranes. Gordeichuk T, et al, 24(1) Ontogenez. 1993 48-55 (1993)

*Panax ginseng* and *Eleutherococcus senticosus* may exaggerate an already existing biphasic response to stress via inhibition of enzymes which limit the binding of stress hormones to their receptors. Specifically, it is suggested that PG inhibits 11-beta hydroxysteroid dehydrogenase one and ES inhibits catechol-O-methyl transferase, both of which reside in close proximity to stress hormone receptors and catalyse the degradation of stress hormones into inactive compounds. In addition, it is suggested that the increased energy said to result from PG and ES may be a consequence of their occupancy of stress hormone receptors. Gaffney B T, Hugel, H M, and Rich, P A, 56(5) Med Hypothesis 567-72 (2001)

Nutritional therapies have included *Vitex agnus-castus*, alpha lipoic acid, glucosamine, folic acid, and standard multiple vitamins.

Only a few published teachings claim to affect this serious and prevalent problem in the population through intervention in the nutritional status of patients. U.S. Patent Application No., 20070104801, to Cecchi, teaches an undescribed fertility enhancing and anti-aging composition that may contain any of alpha-lipoic acid, glucosamine sulfate or Peruvian Maca with or without horny goat weed.

U.S. Pat. No. 7,115,650, to Broqua, teaches a method of improving fertility by the administration of an inhibitor of dipeptidyl peptidase IV, wherein said inhibitor is an amino-acyl pyrrolidine or an amino-acyl thiazolidine.

U.S. Pat. No. 6,569,857, to Hermelin, teaches a method for increasing the possibility of conception while enhancing nutritional stores for a developing embryo or fetus prior to and during pregnancy by administering to an animal during a period commencing prior to at least two weeks before conception a specific dose of vitamin B6 and folic acid.

U.S. Pat. No. 7,410,657, to Lee, teaches several compositions for enhancing fertility that require a large number of herbs used in Chinese medicine, including Radix Polygalae Tenuifoliae, Semen Ziziphi Spinosae, Radix Ginseng, Rhizoma Atractylodis Macrocephalae, Rhizoma Zingiberis Officinalis Recens, Sclerotium Poriae Cocos, Radix Astragali, Radix Ligustici Wallichii, Radix Angelicae Sinensis, and the like.

U.S. Pat. No. 6,989,164, to Trant, teaches a pharmaceutical composition for oral ingestion having fertility promoting activity in males comprising components present in the proportion in parts by weight of: about 5 to 50% green tea, vitamin C, vitamin E, and selenium, about 10 to 80% L-carnitine, up to about 1% ferulic acid in Dong quai, up to about 1% vitamins B6, B12, and folate, up to about 10% zinc. The combination of L-carnitine and Coenzyme Q10, but not *Lepidium* Meyenii, is taught by another patent to Trant, U.S. Pat. No. 7,045,151 for a pharmaceutical composition having fertility promoting activity in males comprising components present in the proportion in parts by weight of about 20 to 80% L-carnitine, about 5 to 30% vitamins C and E, about 0.1 to 10% coenzyme Q10, about 0.001 to 1% selenium, about 0.2 to 20% ferulic acid, about 0.1 to 2% zinc, and about 0.001 to 1% B vitamins.

U.S. Pat. No. 6,861,079, to Sweazy, teaches a fertility kit to enhance natural fertility and detect female ovulation and male fertility potential comprising specific dose ranges of L-Arginine, L-Cysteine, Selenium, Vitamin C, Vitamin E, Zinc, *Astragalus, Pycnogenol*, Vitamin B-6, Para-aminobenzoic acid (PABA), Vitamin A, Folic Acid, at least one phytoestrogen, along with several devices used in the promotion of ovulation timing and intercourse.

U.S. Pat. No. 6,372,266, to Sweezey, teaches the use of resveratrol in infertility. U.S. Patent Application No. 20070099826, to Wong teaches a compound capable of modulating transcription arising from an egr-1 response element consensus sequence and expression state of a gene in manufacture of a medicament for the treatment of a disease or health condition associated with an expression state of a gene associated with an egr-1 response element consensus sequence that may be resveratrol and may be used to treat infertility. Neither of these patents teach the combination of resveratrol with para amino-benzoic acid and red clover extract.

This inventor has discovered the elegant combination of these three nutrients, each with a primary effect on a different aspect of process of conception and pregnancy

SUMMARY OF INVENTION

Pursuant to this invention a new composition and method is described to provide human female infertility therapy.

The present invention describes an alternative therapy for infertility. The effects of the three nutrient components of this composition have been shown by various researchers, but never before has a composition been provided that offers the combined effects of grape seed, para amino-benzoic acid (PABA), and red clover. In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

DETAILED DESCRIPTION OF THE PREFERRED EMBODIMENTS

In the Summary above, the Description of the Invention, and the Claims and Abstract below, reference may be made to particular features (including method steps) of the invention. It is to be understood that this disclosure includes possible combinations of such particular features. For example, where a particular feature is disclosed in the context of a particular aspect or embodiment of the invention, or a particular claim, that feature may also be used, to the extent possible, in combination with and/or in the context of other particular aspects and embodiments of the invention, and in the invention generally.

The term "comprises" and grammatical equivalents thereof are used herein to mean that other components, ingredients, steps etc. are optionally present. For example, an article "comprising" (or "which comprises") components A, B and C can consist of (i.e. contain only) components A, B and C, or can contain not only components A, B and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number or the indefinite article "a" (meaning "one") is used herein to denote the start of a range beginning with that number (which may be a range having an upper limit or no upper limit, depending on the variable being defined). For example "at least one" or "at least a" means 1 or more than 1. The term "at most" followed by a number is used herein to denote the end of a range ending with that number (which may be a range having 1 or 0 as its lower limit or a range having no lower limit, depending upon the variable being defined). For example, "at most 4" means 4 or less than 4, and "at most 40%" means 40% or less than 40%. If, in this disclosure, a range is given as "(a first number) to (a second number)" or "(a first number)-(a second number)", this means a range whose lower limit is the first number and whose upper limit is the second number. For example, 0-10 mm means a range whose lower limit is 0 mm, and whose upper limit is 10 mm.

The term "or" is used herein as a conjunction used to link alternatives in a series of alternatives. The term "and/or" is used herein as a conjunction meaning that either or both of two options may be valid.

"Animal" refers to a human, mammal or any other animal. "Conception" refers to the beginning of pregnancy as marked by the formation of a zygote. "Possibility of conception" refers to the likelihood of conception occurring during normal sexual activity. "Nutritional stores" refers to the levels of vitamins, minerals and other nutrients which will be available for use by the father, mother, developing embryo, fetus and newborn infant. "Nutritional status" refers to the presence or absence of any vitamin or mineral deficiency, or in other words, the extent to which physiological vitamin and mineral demands are being satisfied such that deficiency is avoided.

In the one embodiment of this invention, a fertility-enhancing composition for human female fertility therapy is taught, comprising an interleukin-6 inhibiting dose of grape seed, a dose of PABA sufficient to support and protect blood folic acid levels, and a dose of red clover comprising phytoestrogenic isoflavones. The composition may be in a dosage form of a tablet, capsule, liquid, liposome, inhalant, sublingual tablet, suppository, oral spray and dermal patch and may further comprise a pharmaceutically acceptable carrier.

In a more specific embodiment, the grape seed is present in amount of 2 mg to about 300 mg, the PABA is present in an amount of about 20 mg to about 2000 mg, and the red clover is present in an amount of about 150 mg to about 1500 mg. In an even more specific embodiment, the grape seed is present in an amount of about 5 mg to about 50 mg, the PABA is present in an amount of about 70 mg to about 600 mg, and the red clover is present in an amount of about 150 mg to about 1500 mg. Most specifically, the grape seed is present in amount of about 15 mg, the PABA is present in an amount of about 200 mg, and the red clover is present in an amount of about 450 mg. The PABA is present in an amount of about 70 mg to about 600 mg, The grape seed may contain 90% proanthocyanidins.

The fertility-enhancing composition may comprise at least of one additional nutrient selected from the group consisting of group consisting of *Eleutheros senticocus* and *Ginkgo biloba*, and *Vitex agnus castus*. The *Vitex agnus castus* may be present as a 5:1 extract. In a more specific embodiment, the *Eleutheros senticosus* is present in an amount of about 25 mg to about 2500 mg, the *Ginkgo biloba* is present in an amount of about 3 mg to about 300 mg, and the *Vitex agnus castus* is present in an amount of about 20 mg to about 200 mg. Even more specifically, the *Eleutheros senticosus* is present in an amount of about 100 mg to about 1000 mg, the *Ginkgo biloba* is present in an amount of about 10 mg to about 100 mg, and the *Vitex agnus castus* is present in an amount of about 6 mg to about 600 mg. In its most specific embodiment, the *Eleutheros senticosus* is present in an amount of about 150 mg to about 350 mg, said *Ginkgo biloba* is present in an amount of about 20 mg to about 40 mg, and said *Vitex agnus castus* is present in an amount of about 40 mg to about 80 mg. The *Eleutheros senticosus* may be present as a 5:1 extract the *Ginkgo biloba* extract may be present as a 4:1 extract, and the *Vitex agnux castus* may be present as a 5:1 extract.

The fertility-enhancing composition may further comprise a multi-vitamin comprising Vitamin A, Vitamin C, Vitamin D3, Vitamin E, thiamine, riboflavin, niacin, Vitamin B6, Folic Acid, Vitamin B12, pantothenic acid, iron, iodine, magnesium, zinc, selenium, copper, and Para amino benzoic acid (PABA). More specifically, the Vitamin A is beta carotene in an amount of about 8 mg to about 16 mg, the Vitamin C is ascorbic acid present in an amount of about 50 mg to about 120 mg, the Vitamin D3 is cholicalciferol in an amount of about 2 mg to about 6 mg, the Vitamin E is d-alpha tocopheryl succinate present in amount of about 50 mg to about 150 mg, the thiamine is thiamine hydrochloride and is present in an amount of about 1 mg to about 2 mg, the riboflavin is present in an amount of about 1 mg to about 2.5 mg, the niacin is present in an amount of about 15 mg to about 30 mg, the Vitamin B6 is pyridoxal 5' phosphate and is present in an amount of about 1 mg to about 3 mg, the folic acid is present in an amount of about 400 mcg to about 800 mcg, the Vitamin B12 is methylcobalamin and is present in an amount of about 4 mcg to about 8 mcg, the pantothenic acid is from d-calcium pantothenate and is present in an amount of about 5 mg to about 15 mg, the iron is from iron amino acid chelate and is present in an amount of about 12 to about 25 mg, the iodine is from kelp and is present in an amount of about 100 mcg to about 200 mcg, the magnesium is present as magnesium oxide and is present in an amount of about 100 mg to about 400 mg, the zinc is zinc gluconate and is present in an amount of about 10 mg to about 20 mg, the selenium is selenomethionine and is present in an amount of about 50 mcg to about 100 mcg, and the copper is copper gluconate and is present in an amount of about 1 mg to about 3 mg.

In yet another embodiment, the fertility-enhancing composition for female fertility therapy consists of about 1 mg to 500 mg of grape seed, about 20 mg to about 2000 mg of PABA, about 50 mg to about 5000 mg of clover, about 25 mg to about 2500 mg of *eleutheros senticosus*, about 3 mg to about 300 mg of *Ginkgo biloba*, about 5 mg to about 600 mg of *Vitex agnus castus*, about 1 mg to about 120 mg Vitamin A, about 8 mg to about 1000 mg of Vitamin C, about 1 mg to about 40 mg of Vitamin D3, about 10 mg to about 1000 mg of Vitamin E, about 1 mcg to about 15 mg thiamine, about 2 mg to about 200 mg of niacin, about 0.2 mg to about 200 mg of Vitamin B6, about 60 mcg to about 6 mg of folic acid, about 60 mcg to about 6 mg of Vitamin B12, about 1 mg to about 100 mg of pantothenic acid, about 15 mcg to about 1.5 mg of iodine, about 30 mg to about 3000 mg of magnesium, about 1 mg to about 150 mg of zinc, about 7 mcg to about 700 mcg of selenium, and about 200 mcg to about 20 mg of copper.

In yet another specific embodiment, the fertility-enhancing composition for female infertility consists of about 5 mg to about 30 mg of grape seed, about 100 mg to about 300 mg of PABA, about 150 mg to about 1500 mg of Red clover, about 100 mg to about 1000 mg of *Eleutheros senticosus*, about 10 mg to about 100 mg of *Ginkgo biloba*, about 20 mg to about 200 mg of *Vitex agnus castus*, about 4 mg to about 40 mg of Vitamin A, about 25 mg to about 250 mg of Vitamin C, about 1 mg to about 12 mg of Vitamin D3, about 30 mg to about 300 mg of Vitamin E, about 0.5 mg to about 50 mg of thiamine, about 0.5 mg to about 5 mg of riboflavin, about 6 mg to about 60 mg of niacin, about 1 mg to about 6 mg of Vitamin B6, about 200 mcg to about 2 mg of folic acid, about 2 mcg to about 20 mcg of Vitamin B12, about 3 mg to about 30 mg of pantothenic acid, about 6 mg to about 60 mg of iron, about 50 mcg to about 400 mcg of iodine, about 100 mg to about 1000 mg of magnesium, about 5 mg to about 50 mg of zinc, about 20 mcg to about 200 mcg of selenium, and about 1 mg to about 6 mg of copper.

In its most specific embodiment, the fertility-enhancing composition for female infertility consists of about 10 mg to about 20 mg of grape seed present as extract, about 300 mg to about 600 mg of Red clover present as extract, about 150 mg to about 400 mg of *Eleutheros senticosus* present as extract, about 40 mg to about 80 mg of *Vitex agnus-chaste* present as extract, about 20 mg to about 40 mg of *Ginkgo biloba* present as extract, about 8 mg to about 16 mg of Vitamin A present as beta carotene, about 50 mg to about 120 mg of Vitamin C present as ascorbic acid, about 2 mg to about 6 mg of Vitamin D3 present as cholicalciferol, about 50 mg to about 150 mg of Vitamin E present as d-alpha tocopheryl succinate, about 1 mg to about 2 mg of thiamine, about 1 mg to about 2.5 mg of riboflavin, about 15 mg to about 30 mg of niacin, about 1 mg to about 3 mg of Vitamin B6 present as pyridoxal 5' phosphate, about 400 mcg to about 800 mcg of folic acid, about 4 mcg to about 8 mcg of Vitamin B12 present as methylcobalamin, about 5 mg to about 15 mg pantothenic acid, about 12 mg to about 25 mg of iron from iron amino acid chelate, about 100 mcg to about 200 mcg of iodine from kelp, about 100 mg to about 400 mg of magnesium present as magnesium oxide, about 10 mg to about 20 mg of zinc present as zinc gluconate, about 50 mcg to about 100 mcg of selenium present as selenomethionine, and about 1 mg to about 3 mg of copper present as copper gluconate.

Also taught are methods of enhancing fertility in a female human in need thereof by inhibiting interleukin-6, stimulating progesterone, and providing phytoestrogenic isoflavones by administering an effective amount of the fertility enhancing composition of grape seed, para amino-benzoic acid, and red clover to a patient in need of treatment thereof. Any of the specific dose ranges and dosages set forth in the various embodiments may be used. The administration may be in one to three doses per day and is continued until conception is achieved or for at least 3 months. The method may further include the administration of an appropriate fertility enhancing composition to the male partner of the female human.

The invention is described by the following non-limiting example:

Example 1

Ninety female patients with infertility are orally administered 15 mg of grape seed, 200 mg of para amino-benzoic acid (PABA), and 450 mg of red clover. The grape seed contains 90% proanthocyanidins and ninety female patients with infertility are orally administered placebo. Eighty of the 90 patients in the active treatment group and 75 of the controls finish the three month treatment period. At the end of the period, female spouses of 10 patients (12.5%) achieve pregnancy. Moreover, their levels of Interleukin-6 are decreased significantly and their luteal phase progesterone is increased significantly (P<0.01). In control group, only two pregnancies, (2.6%) are observed, which is statistically significant (P<0.05>)

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A fertility enhancing composition for human female fertility therapy comprising an interleukin-6 inhibiting dose of grape seed, a dose of para-amino benzoic acid (PABA) protective of folic acid levels, and a dose of red clover comprising phytoestrogenic isoflavones, at least of one additional nutrient selected from the group consisting of *Eleutherococcus senticocus, Ginkgo biloba*, and *Vitex agnus castus*, and Vitamin A as beta carotene in an amount of about 8 mg to about 16 mg, Vitamin C as ascorbic acid in an amount of about 50 mg to about 120 mg, Vitamin D3 as cholecalciferol in an amount of about 2 mg to about 6 mg, Vitamin E as d-alpha tocopheryl succinate in amount of about 50 mg to about 150 mg, thiamine as thiamine hydrochloride and in an amount of about 1 mg to about 2 mg, riboflavin in an amount of about 1 mg to about 2.5 mg, niacin in an amount of about 15 mg to about 30 mg, Vitamin B6 as pyridoxal 5'-phosphate and in an amount of about 1 mg to about 3 mg, folic acid in an amount of about 400 mcg to about 800 mcg, Vitamin B12 as methylcobalamin and in an amount of about 4 mcg to about 8 mcg, pantothenic acid from d-calcium pantothenate and in an amount of about 5 mg to about 15 mg, iron from iron amino acid chelate and in an amount of about 12 mg to about 25 mg, iodine from kelp and in an amount of about 100 mcg to about 200 mcg, magnesium as magnesium citrate and in an amount of about 50 mg to about 700 mg, zinc as zinc gluconate and in an amount of about 10 mg to about 20 mg, selenium as selenomethionine and in an amount of about 50 mcg to about 100 mcg, and copper as copper gluconate and in an amount of about 1 mg to about 3 mg.

2. A fertility-enhancing composition for female fertility therapy consisting of about 1 mg to 500 mg of grape seed, about 20 mg to about 2000 mg of PABA, about 50 mg to about 2000 mg of red clover, about 10 mg to about 1500 mg of *Eleutherococcus senticosus, about* 3 mg to about 300 mg of *Ginkgo biloba*, about 5 mg to about 600 mg of *Vitex agnus castus*, about 1 mg to about 120 mg Vitamin A, about 8 mg to about 1000 mg of Vitamin C, about 1 mg to about 40 mg of Vitamin D3, about 10 mg to about 1000 mg of Vitamin E, about 1 mcg to about 15 mg thiamine, about 2 mg to about 200 mg of niacin, about 0.2 mg to about 200 mg of Vitamin B6, about 60 mcg to about 6 mg of folic acid, about 60 mcg to about 6 mg of Vitamin B12, about 1 mg to about 100 mg of pantothenic acid, about 15 mcg to about 1.5 mg of iodine, about 10 mg to about 1000 mg of magnesium, about 1 mg to about 150 mg of zinc, about 7 mcg to about 700 mcg of selenium, and about 200 mcg to about 20 mg of copper.

3. The fertility-enhancing composition for female fertility therapy consisting of about 5 mg to about 30 mg of grape seed, about 100 mg to about 300 mg of PABA, about 100 mg to about 600 mg of Red clover, about 100 mg to about 700 mg of *Eleutherococcus senticosus*, about 10 mg to about 100 mg of *Ginkgo biloba*, about 20 mg to about 200 mg of *Vitex agnus castus*, about 4 mg to about 40 mg of Vitamin A, about 25 mg to about 250 mg of Vitamin C, about 1 mg to about 12 mg of Vitamin D3, about 30 mg to about 300 mg of Vitamin E, about 0.5 mg to about 50 mg of thiamine, about 0.5 mg to about 5 mg of riboflavin, about 6 mg to about 60 mg of niacin, about 1 mg to about 6 mg of Vitamin B6, about 200 mcg to about 2 mg of folic acid, about 2 mcg to about 20 mcg of Vitamin B12, about 3 mg to about 30 mg of pantothenic acid, about 6 mg to about 60 mg of iron, about 50 mcg to about 400 mcg of iodine, about 50 mg to about 700 mg of magnesium, about 5 mg to about 50 mg of zinc, about 20 mcg to about 200 mcg of selenium, and about 1 mg to about 6 mg of copper.

4. The fertility-enhancing composition for female fertility therapy consisting of about 10 mg to about 20 mg of grape seed present as extract, about 200 mg to about 400 mg of Red clover present as extract, about 100 mg to about 300 mg of *Eleutherococcus senticosus* present as extract, about 40 mg to about 80 mg of *Vitex agnus-chaste* present as extract, about 20 mg to about 40 mg of *Ginkgo biloba* present as extract, about 8 mg to about 16 mg of Vitamin A present as beta carotene, about 50 mg to about 120 mg of Vitamin C present as ascorbic acid, about 2 mg to about 6 mg of Vitamin D3 present as cholecalciferol, about 50 mg to about 150 mg of Vitamin E present as d-alpha tocopheryl succinate, about 1 mg to about 2 mg of thiamine, about 1 mg to about 2.5 mg of riboflavin, about 15 mg to about 30 mg of niacin, about 1 mg to about 3 mg of Vitamin B6 present as pyridoxal 5'-phosphate, about 400 mcg to about 800 mcg of folic acid, about 4 mcg to about 8 mcg of Vitamin B12 present as methylcobalamin, about 5 mg to about 15 mg pantothenic acid, about 12 mg to about 25 mg of iron from iron amino acid chelate, about 100 mcg to about 200 mcg of iodine from kelp, about 100 mg to about 300 mg of magnesium present as magnesium citrate, about 10 mg to about 20 mg of zinc present as zinc gluconate, about 50 mcg to about 100 mcg of selenium present as selenomethionine, and about 1 mg to about 3 mg of copper present as copper gluconate.

\* \* \* \* \*